United States Patent [19]

Onodera et al.

[11] Patent Number: 4,822,782
[45] Date of Patent: Apr. 18, 1989

[54] METHOD FOR TREATING AIDS USING STREPTOVARICIN C COMPOUNDS

[75] Inventors: Kazukiyo Onodera, Tokyo; Shinichi Ito, Tokorozawa, both of Japan

[73] Assignee: Shin-Etsu Chemical Co., Ltd., Tokyo, Japan

[21] Appl. No.: 137,823

[22] Filed: Dec. 24, 1987

[30] Foreign Application Priority Data

Dec. 27, 1986 [JP] Japan .................................. 61-313463

[51] Int. Cl.⁴ .................... A61K 31/395; C07D 491/08
[52] U.S. Cl. ....................................... 514/183; 540/456
[58] Field of Search ......................... 540/456; 514/183

[56] References Cited

U.S. PATENT DOCUMENTS 4,212,881 7/1980 Sasaki et al. ...................... 540/456

OTHER PUBLICATIONS

Miyoshi et al., *Nature*, vol. 294, No. 5843, Dec. 1981, pp. 770–771.

*Primary Examiner*—Mary C. Lee
*Assistant Examiner*—Zinna Northington

*Attorney, Agent, or Firm*—Oblon, Fisher, Spivak, McClelland & Maier

[57] ABSTRACT

An anti-AIDS virus agent comprising as an effective component a streptovaricin C derivative represented by the general formula (I):

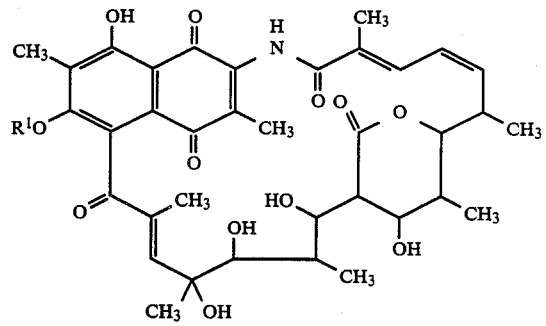

wherein $R^1$ represents an alkyl group having 3 to 7 carbon atoms.

The streptovaricin C derivative has good HIV-growth inhibiting activity, and this agent is useful for therapy of AIDS.

2 Claims, 1 Drawing Sheet

METHOD FOR TREATING AIDS USING STREPTOVARICIN C COMPOUNDS

BACKGROUND OF THE INVENTION

1. Field of the Invention

This invention relates to an anti-AIDS virus agent.

2. Description of the Prior Art

Any effective therapeutic method for acquired immune deficiency syndrome (AIDS) has not yet been established.

U.S. Pat. No. 4,212,881 discloses that streptovaricin C derivatives represented by the general formula

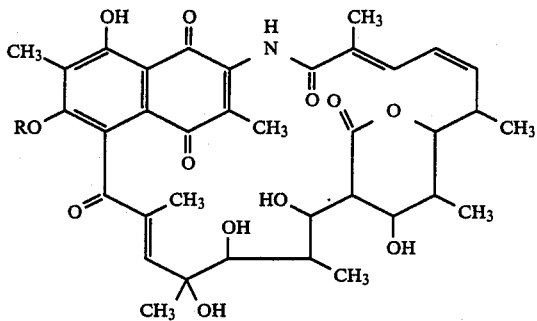

wherein R represents an allyl, cyclopentyl, cyclohexyl or adamanthyl group or a $C_1, -C_{20}$ alkyl group which can be substituted with hydroxyl, cyano, acetyl, formyl, furoyl, thenoyl, methoxy, carbamyl, phenyl or phenyl group substituted with nitro or ethyl or a phenacyl group which can be substituted with a halogen, methoxy or phenyl group, have anti-tumour virus activities in mice. However, it has not hitherto been known that any of these streptovaricin C derivatives have activities inhibiting growth of virulent virus (HIV) of AIDS.

SUMMARY OF THE INVENTION

The present inventors have discovered that a certain kind of the streptovaricin C derivatives described above has excellent HIV growth-inhibiting activities.

Based on the above discovery, an object of the present invention lies in providing a novel anti-AIDS virus agent useful for therapy of AIDS.

Another object of the present invention is to provide a method for treating AIDS, and a further object is to provide a use of a compound or a composition containing the compound for the manufacture of a medicament for therapy of AIDS.

Thus the present invention provides an anti-AIDS virus agent comprising, in an effective amount, a streptovaricin C derivative represented by the general formula (I):

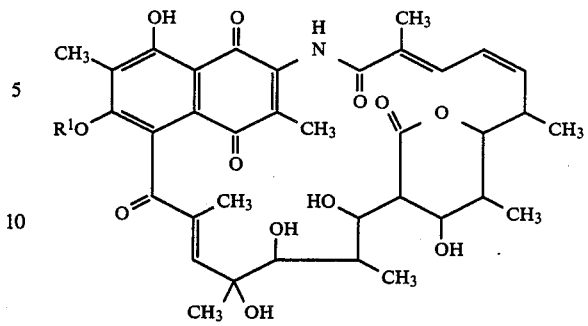

wherein $R^1$ represents an alkyl group having 3 to 7 carbon atoms.

The present invention also provides a method for treating AIDS with use of said streptovaricin C derivative. And the invention provides a use of said streptovaricin C derivative for manufacture of a medicament for therapy of AIDS.

The streptovaricin C derivative used in the present invention has activities remarkably inhibiting HIV growth, and thus the agent of this invention is useful for therapy of AIDS.

DETAILED DESCRIPTION OF THE INVENTION

Figure 1:
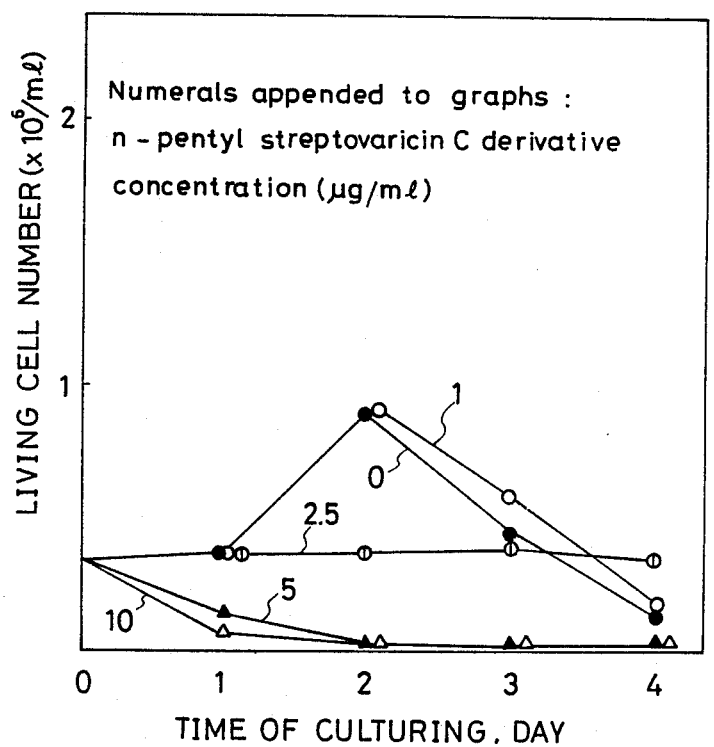
FIG. 1 illustrates the results of culturing of HIV-infected MT-4 cells in the presence of n-pentylstreptovaricin C derivative in various concentrations, as obtained in example.

Examples of the alkyl group having 3 to 7 carbon atoms in the definition of $R^1$ in the general formula (I) include a propyl, butyl, pentyl, hexyl and heptyl group. Preferred is n-pentyl group.

The streptovaricin C derivative of the general formula (I) has low toxicities against HIV-noninfected mammalian cells, and also in this point, the anti-AIDS virus agent of the present invention is excellent.

The streptovaricin C derivative of the general formula (I) has extremely low acute toxicities, and for example, in the case of the derivative having methyl group as the $R^1$ at C-19 position in the general formula (I), 50% lethal dose ($LD_{50}$) against mouse is 1,000 mg/kg or more in intramuscular administration and 3,000 mg/kg or more in oral administration.

The streptovaricin C derivative of the general formula (I) as used in the present invention itself is known, for example, in U.S. Pat. No. 4,212,881, and preparation, isolation and purification thereof can be carried out according to the methods described in the patent.

According to the preparation method disclosed in the above U.S. Pat. No. 4,212,881, the streptovaricin C derivative of the general formula (I) can be prepared by hydrolysis of streptovaricin C in a mild oxidizing condition to produce a streptovaricin C derivative corresponding the compound of the general formula (I) wherein $R^1$ is hydroxyl group together with damavaricin C, and subjecting the streptovaricin C derivative thus obtained to etherification of the phenolic hydroxyl group at the C-19 position.

The streptovaricin C derivative of the general formula (I) is generally obtained in the form of a mixture of two kinds of optical isomers known as damavaricin Fc derivative and atropisodamavaricin Fc derivative. The damavaricin Fc derivative has P-helicitic structure in which a double bond of C(15)=C(16) is disposed at upper side of carbonyl group C(24)=O in stereomatic structure to the single bond C(17)-C(18) in the same manner as in streptovaricin C, whereas atropisodamavaricin Fc has M-helicitic structure in which the double bond is stereomatically in opposite position.

The anti-AIDS virus agent of the present invention may variously be prepared as a pharmaceutical composition by compounding said streptovaricin C derivative with, for example, organic or inorganic solid or liquid vehicles. Examples of preferred vehicles include water, gelatin, lactose, starch, calcium carboxymethylcellulose, microcrystalline cellulose, stearyl alcohol, magnesium stearate, talc, vegetable oils, benzyl alcohol, propylene glycol, gum, polyalkylene glycol, white petrolatum, jelly, cholesterol and the like. Pharmaceuticals thus prepared may be in any form such as powder, tablet, granule, sugar-coated tablet, suppository, pill, capsule, liquid, suspension, ampoule, emulsion and injection. These pharmaceutical compositions may contain various adjuvants, for example, preservatives, stabilizers, wetting agents, emulsifying agents, solubilizing agents, salts for osmotic pressure adjustment, buffers, binding agents, suspending and dispersing agents, lubricants and the like, and can conventionally be prepared.

The desirable dose of the anti-AIDS virus agent of the present invention depends on, for example, race, age, body weight and the like as well as administration method. The dose thereof per day for an adult is generally 1 to 100 mg/kg, preferably 5 to 50 mg/kg in the case of parenteral administration, and is generally 1 to 1,000 mg/kg, preferably 25 to 500 mg/kg in the case of oral administration, respectively as the streptovaricin C derivative of the general formula (I).

The present invention is explained in detail below by an example.

EXAMPLES (1) HTLV-I infected human lymphocyte known as MT-4 (see Miyoshi, I. et al., Nature 294 p. 770 (1981)) was used for testing below. MT-4 cells were infected with HIV of m.o.i. 0.02 according to the Harada et al. method (Harada, S. et al., Science 229, 563 (1985)). The MT-4 cells were then suspended at a concentration of $5 \times 10^5$ cells/ml in each of five kinds of 10% fetal bovine serum-supplemented 1640 media each containing 0, 1, 2.5, 5 or 10 μg/ml of n-pentylstreptovaricin C derivative (the compound of the general formula (I) wherein R is n-pentyl group), and cultured at 37° C. under 5% $CO_2$. Suspended cells were sampled at regular intervals, subjected to trypan blue staining and measured for living cell number and dead cell number with a microscope. Changes of the living cell number in the media thus determined are shown in FIG. 1.

As FIG. 1 shows, in concentrations of n-pentylstreptovaricin C derivative of 1 μg/ml or less, the number of the living MT-4 cells initially increased and then rapidly decreased from 3 days after the start of the culturing. In 2.5 μg/ml, the living cell number was almost unchanged during the culturing, and in 5 μg/ml or more, the living cell number rapidly decreased and the cells almost completely died out 2 days after the start of the culturing.

(2) In another culturing of MT-4 cells infected with HIV of m.o.i. 0.06 conducted similarly to the above, expression of HIV antigen was measured according to the indirect fluorescent antibody technique using AIDS patient serum antibody as a primary antibody (Hinuma, Y. et al., Proc. Natl. Acad. Sci. U.S.A., 78, 6476 (1981)).

As the results, three days after the start of culturing, proportion of the antigen expression cells among the cells infected with HIV reached 80% or more in the case of the culturing in 1 μg/ml or less of n-pentylstreptovaricin C derivative. The proportion was around 20% in the case of the culturing in 2.5 μg/ml, and 0% in the case of the culturing in 5 μg/ml or more.

It can be understood from the above results that n-pentylstreptovaricin C derivative exhibits HIV growth-inhibiting activity at concentration of 2.5 μg/ml or more, and a remarkable inhibiting activity at a concentration of 5 μg/ml or more. It is considered that the cause that the living cell number rapidly decreased from 3 days after start of the culturing in 1 μg/ml or less of n-pentyldamavaricin Fc in FIG. 1 lies in cell destruction due to HIV growth.

What we claim is:

1. A method for treating acquired immune deficiency syndrome which comprises treating a patient suffering from HIV infection with an effective dose of a damavaricin Fc derivative represented by the formula (I):

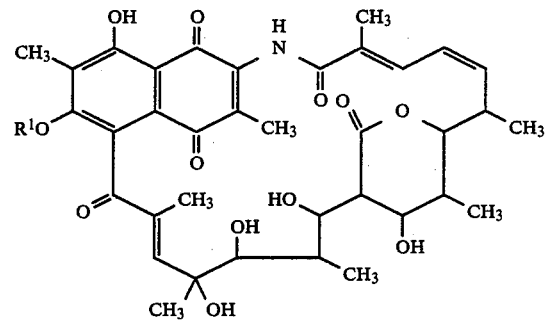

wherein $R^1$ represents an alkyl group having 3 to 7 carbon atoms.

2. The method of claim 1, wherein $R^1$ in the formula (I) is n-pentyl group.

* * * * *